United States Patent
Jun et al.

(10) Patent No.: US 10,214,469 B2
(45) Date of Patent: Feb. 26, 2019

(54) METHOD FOR PRODUCING HIGH-EFFICIENCY METHANOL CAPABLE OF REDUCING EMISSION OF CARBON DIOXIDE

(71) Applicant: KOREA RESEARCH INSTITUTE OF CHEMICAL TECHNOLOGY, Daejeon (KR)

(72) Inventors: Ki Won Jun, Daejeon (KR); In Hyuck Choi, Seoul (KR); Chun Dong Zhang, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 53 days.

(21) Appl. No.: 15/502,134

(22) PCT Filed: Jul. 2, 2015

(86) PCT No.: PCT/KR2015/006808
§ 371 (c)(1),
(2) Date: May 16, 2017

(87) PCT Pub. No.: WO2016/021836
PCT Pub. Date: Feb. 11, 2016

(65) Prior Publication Data
US 2017/0362147 A1 Dec. 21, 2017

(30) Foreign Application Priority Data

Aug. 4, 2014 (KR) ........................ 10-2014-0099569

(51) Int. Cl.
*C07C 29/152* (2006.01)
*C07C 29/151* (2006.01)
(Continued)

(52) U.S. Cl.
CPC .............. *C07C 29/152* (2013.01); *C01B 3/38* (2013.01); *C07C 4/02* (2013.01); *C07C 4/06* (2013.01);
(Continued)

(58) Field of Classification Search
None
See application file for complete search history.

(56) References Cited

U.S. PATENT DOCUMENTS

| | | | |
|---|---|---|---|
| 6,100,303 A * | 8/2000 | Hirotani | ................ C01B 3/382 518/700 |
| 6,218,439 B1 | 4/2001 | Kobayashi et al. | |
| 2003/0022948 A1 | 1/2003 | Seiki et al. | |

FOREIGN PATENT DOCUMENTS

| | | |
|---|---|---|
| EP | 0926096 A1 | 6/1999 |
| EP | 1008577 A1 | 6/2000 |

(Continued)

OTHER PUBLICATIONS

International Preliminary Report on Patentability, dated Feb. 7, 2017 with an English Translation of Written pinion of the International Searching Authority of Sep. 25, 2015, for PCT/KR2015/006808.

(Continued)

*Primary Examiner* — Medhanit W Bahta
(74) *Attorney, Agent, or Firm* — Hauptman Ham, LLP

(57) ABSTRACT

A method for producing high-efficiency methanol capable of reducing emission of carbon dioxide. The method includes: a first step of preparing mixed gas by using steam and natural gas as raw materials and converting $C_{2+}$ hydrocarbon contained in the natural gas into methane on a catalyst; a second step of preparing a synthesis gas including carbon monoxide, carbon dioxide, and hydrogen by reforming the mixed gas in a reformer filled with a reforming catalyst; and (Continued)

a third step of preparing methanol by using the synthesis gas as the raw material and reacting the synthesis gas.

18 Claims, 6 Drawing Sheets

(51) Int. Cl.
- *C07C 29/153* (2006.01)
- *C07C 29/74* (2006.01)
- *C07C 31/04* (2006.01)
- *C07C 4/06* (2006.01)
- *C01B 3/38* (2006.01)
- *C07C 4/02* (2006.01)

(52) U.S. Cl.
CPC .......... *C07C 29/151* (2013.01); *C07C 29/153* (2013.01); *C07C 29/74* (2013.01); *C07C 31/04* (2013.01); *C01B 2203/0233* (2013.01); *C01B 2203/0238* (2013.01); *C01B 2203/061* (2013.01); *C01B 2203/107* (2013.01); *C01B 2203/1058* (2013.01); *C01B 2203/1064* (2013.01); *C01B 2203/142* (2013.01); *Y02P 20/124* (2015.11); *Y02P 20/142* (2015.11); *Y02P 20/582* (2015.11)

(56) References Cited

FOREIGN PATENT DOCUMENTS

| | | | |
|---|---|---|---|
| EP | 1277697 | A2 | 1/2003 |
| JP | 2001122811 | A | 5/2001 |
| JP | 2002-60357 | A | 2/2002 |
| JP | 2003034660 | A | 2/2003 |
| JP | 2013-119526 | A | 6/2013 |
| KR | 10-2010-0014012 | A | 2/2010 |
| KR | 10-0991263 | B | 2/2010 |
| KR | 10-1085038 | B | 2/2010 |
| KR | 1020100065504 | A | 6/2010 |
| KR | 101068995 | B1 | 9/2011 |
| WO | 2004/088225 | A2 | 10/2004 |
| WO | 2014/096226 | A1 | 6/2014 |

OTHER PUBLICATIONS

International Search Report dated Sep. 25, 2015, corresponding to International Publication No. PCT/KR2015/006808.

Extended European Search Report dated Jun. 12, 2017 from European Patent Office in connection with the counterpart European Patent Application No. 15829483.5.

Korean Office Action dated Jun. 13, 2017 from KIPO in connection with the counterpart Korean Patent Application No. 10-2014-0099569.

* cited by examiner

METHOD FOR PRODUCING HIGH-EFFICIENCY METHANOL CAPABLE OF REDUCING EMISSION OF CARBON DIOXIDE

This present application is a national stage filing under 35 U.S.C § 371 of PCT application number PCT/KR2015/006808 filed on Jul. 2, 2015 which is based upon and claims the benefit of priority to Korean Patent Application Nos. 10-2014-0099569 filed on Aug. 4, 2014 in the Korean Intellectual Property Office. The disclosures of the above-listed applications are hereby incorporated by reference herein in their entirety.

TECHNICAL FIELD

The present invention relates to a method for producing methanol, and more particularly, to a method for producing methanol, which can increase utilization efficiency of carbon dioxide as a reactant and synthesis yield of methanol and simultaneously achieve minimization of emission of carbon dioxide and maximization of the process thermal efficiency.

BACKGROUND ART

Since the Kyoto Protocol on the reduction of carbon dioxide emissions has entered into force globally since 2005 due to the seriousness of global warming, there have been various studies on the efficient utilization of carbon dioxide, as well as the development of technologies to reduce carbon dioxide emissions.

As a technology to utilize carbon dioxide, a method has been studied, in which synthesis gas is produced by performing steam and carbon dioxide reforming of natural gas (SCR) and useful chemical raw materials (e.g., methanol, dimethyl ether, etc.,) are produced by using the synthesis gas as a raw material.

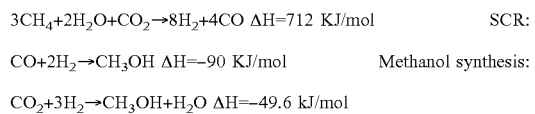

U.S. Pat. No. 6,100,303 discloses a method for achieving reduced construction cost of a process and improved energy efficiency by using combustion type and heat exchanger type reformers which are two different types of reformers in a steam reforming process of natural gas and using some (purge gas) of unreacted gas as a raw material for reforming/methanol synthesis units and also as the fuel gas of the reformer, as a method for improving energy efficiency and $CO_2$ utilization.

Further, U.S. Pat. No. 6,218,439 discloses a process for minimizing an emission amount of $CO_2$ by re-inputting $CO_2$ formed during steam reforming process into the reformer or methanol synthesis reactor after separation process as a utilization scheme of $CO_2$ generated during the reaction.

However, a natural gas reforming method and a recycling method, which are presented in the above patents, are different from the methods used in the present invention. In particular, a layout of a heat exchanger used in the present invention is never disclosed.

DISCLOSURE

Technical Problem

An object of the present invention is to provide a method for producing methanol from natural gas, which can optimize carbon efficiency and heat efficiency through minimization of emission of carbon dioxide per unit amount of methanol production by introducing an appropriate recycling method of an unreacted material and appropriately reusing heat generated in a process while supplying an appropriate amount of carbon dioxide in a methanol production process in which methanol is synthesized from the natural gas and carbon dioxide.

Technical Solution

In order to solve the problem, the present invention provides a method for producing methanol, including: a first step of preparing mixed gas by using steam and natural gas as reaction feed materials and converting $C_{2+}$ hydrocarbon contained in the natural gas into methane on a catalyst; a second step of preparing a synthesis gas including carbon monoxide, carbon dioxide, and hydrogen by reforming the mixed gas in a reformer filled with a reforming catalyst; and a third step of preparing methanol by using the synthesis gas as a raw material and reacting the synthesis gas in a methanol synthesis reactor filled with a methanol synthesis catalyst, after which the methanol as a product in the methanol synthesis process and unreacted synthesis gas are separated, some of the separated unreacted synthesis gas is supplied to a heating furnace providing reaction heat required by the reformer of the second step and combusted together with the natural gas, and the mixed gas supplied to the reformer passes through a heat exchanger, exchanging heat with the post-combustion gas emitted from the heating furnace, to transfer the heat from the post-combustion gas to the mixed gas entering the reformer.

Advantageous Effects

By a method for producing methanol according to the present invention, natural gas is reacted with steam such that $C_{2+}$ hydrocarbon in the natural gas is converted into methane to produce mixed gas, carbon dioxide is introduced into a reforming reaction to manufacture synthesis gas of which the composition is controlled from the mixed gas or carbon dioxide is introduced into a methanol synthesis reaction to be used for methanol synthesis, and an unreacted gas is recycled to reforming and methanol synthesis units to be reused as a raw material, thereby reducing emission of carbon dioxide and increasing production of methanol.

Further, by the production method according to the present invention, for supplying heat required by the reformer, the heat of high-temperature gas obtained by fuel gas combustion in a heating furnace is recovered by using a heat exchangers, such that the energy efficiency of the whole process is improved.

EXPLANATION OF REFERENCE NUMERALS AND SYMBOLS

11: Pre-reformer
13: Reformer
14: Heating furnace
15: Methanol synthesis reactor
17: Separator
19: Splitter
E-101: Seventh heat exchanger
E-102: Sixth heat exchanger
E-103: Fifth heat exchanger
E-104: Fourth heat exchanger
E-105A: First heat exchanger
E-105B: Second heat exchanger
E-107: Eighth heat exchanger
E-108: Third heat exchanger

BEST MODE

The present invention will be described below in more detail.

The present invention relates to a method for synthesizing methanol from natural gas, which may minimize a generation amount of carbon dioxide per unit amount of methanol production and optimize carbon efficiency and thermal efficiency by introducing a recycling method of an unreacted material and reusing heat generated in a process by an optimal method while supplying an appropriate amount of carbon dioxide before or after a reforming reaction in using a prior research result (Korean Patent Registration No. 10-0991263) of the present inventor, which may manufacture synthesis gas which is advantageous in a methanol synthesis reaction by performing steam carbon dioxide reforming of methane (SCR) that simultaneously performs steam reforming of methane (SRM) (Korean Patent Registration No. 10-1068995) and carbon dioxide reforming of methane (CDR) of natural gas, and a prior research result (Korean Patent Registration No. 10-1085038) of the present inventor, which is developed as a catalyst to suppress generation of a by-product in methanol synthesis from synthesis gas.

Figure 1A:
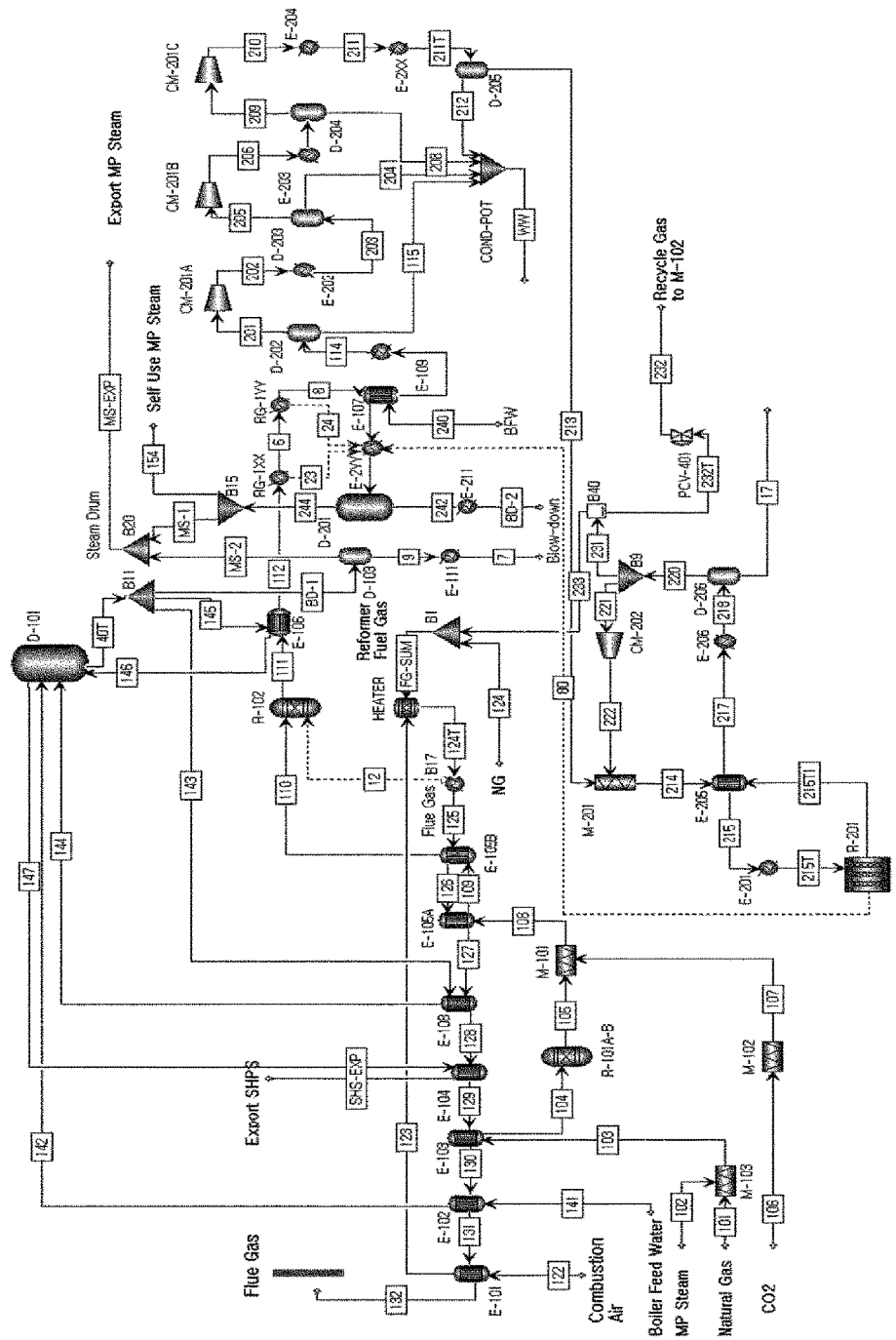
FIGS. 1A and 1B are schematic views illustrating a configuration of reforming reaction and methanol synthesis processes in the present invention.
Figure 1B:
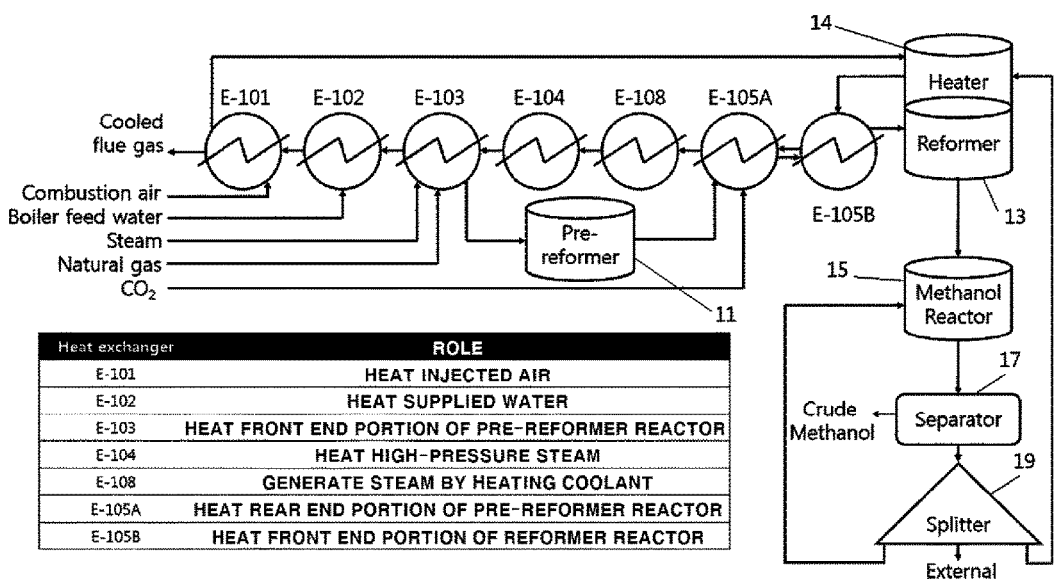

FIG. 1A is a schematic view illustrating a facility of reforming reaction and methanol synthesis processes in the present invention and FIG. 1B is a schematic view illustrating primary components thereof.

Figure 2A:
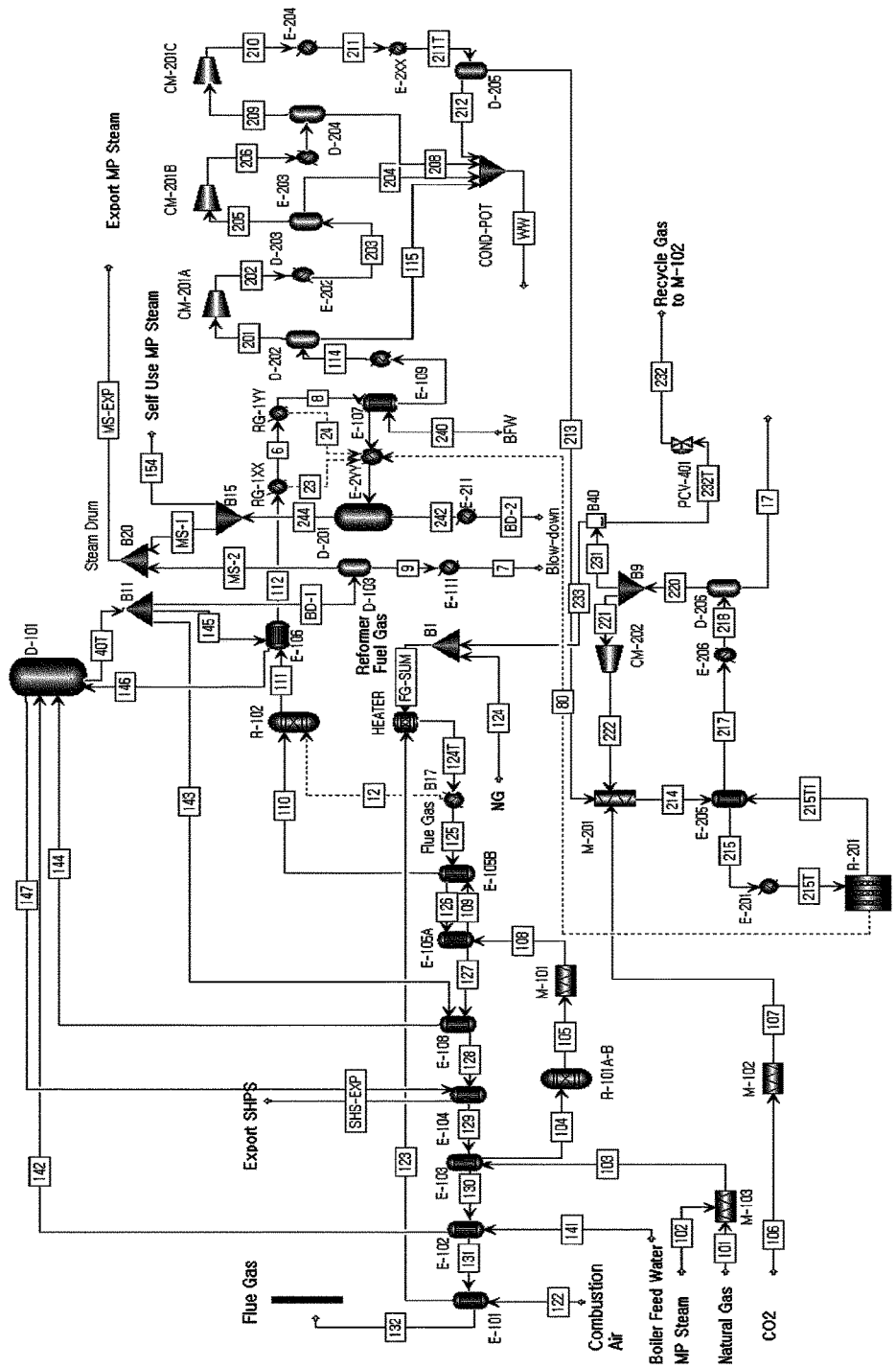
FIGS. 2A and 2B are schematic views illustrating a configuration of reforming reaction and methanol synthesis processes in which carbon dioxide injection position is adjusted in the present invention.
Figure 2B:
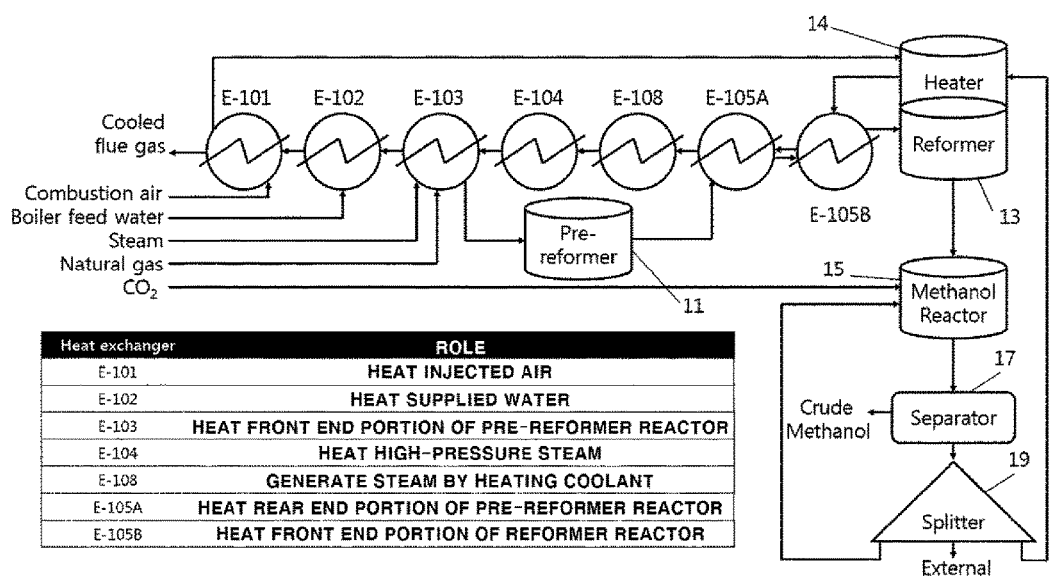

Further, FIG. 2A is a schematic view illustrating a facility of reforming reaction and methanol synthesis processes in which a carbon dioxide injection position is adjusted in the present invention and FIG. 2B is a schematic view illustrating primary components thereof.

The method for synthesizing methanol according to the present invention includes a first step of preparing a mixed gas by using natural gas and steam as raw materials and converting $C_{2+}$ hydrocarbon contained in the natural gas into methane on a catalyst, a second step of preparing a synthesis gas, in which a mole ratio of hydrogen to carbon monoxide to carbon dioxide is adjusted, from the mixed gas, and a third step of synthesizing methanol on the catalyst using the synthesis gas as a raw material, and an unreacted synthesis gas emitted in the methanol synthesis process is recycled to the second step and the third step at the same time or only to the third step to be reused as a raw material of a methanol synthesis reaction.

In the mixed gas preparing step which is the first step, a pre-reformer 11 for a mixed reforming reaction is used and the pre-reformer 11 is connected to a rear end portion of a pre-heater (a heat exchanger of E-103 in FIGS. 1A and 1B, 2A and 2B, and 3A and 3B).

In the mixed gas preparing step, the natural gas and the steam are supplied to the pre-reformer 11, and the pre-reformer 11 converts the $C_{2+}$ hydrocarbon included in the natural gas into methane on the catalyst to prepare the mixed gas.

In this case, the natural gas and the steam supplied to the pre-reformer 11 pass through the heat exchanger (the heat exchanger of E-103 in FIGS. 1A and 1B, 2A and 2B, and 3A and 3B) which becomes the pre-heater and the natural gas and the steam which are the raw materials are combusted at a high temperature and thereafter, are heated through heat exchange with gas in the heat exchanger E-103 and then are supplied to the pre-reformer 11.

Herein, the aforementioned high temperature gas after combustion refers to the emitted gas from the furnace 14 in which the gas emitted from the methanol synthesis process is mixed with the natural gas used as fuel and then mixed gas is combusted. The high-temperature gas after combustion passes through a series of heat exchangers, the natural gas and the steam which are raw materials are pre-heated in the heat exchanger of E-103 and the heated natural gas and the heated steam are supplied to the pre-reformer 11.

Before the mixed reforming reaction, a sulfur compound included in the natural gas is pre-treated in order to suppress the deactivation of a reforming catalyst by pre-removing a sulfur component in the natural gas by using an adsorptive desulphurization method or a hydro-desulphurization method which is a generally well-known technology.

In the pre-reformer 11 used for preparing the mixed gas, most $C_{2+}$ hydrocarbon (ethane, propane, butane, etc.,) included in the natural gas is converted into methane by a metal catalyst including nickel, and as a result, in a subsequent process, the reforming reaction proceeds suppressing carbon deposition, which ultimately causes the catalyst deactivation.

Further, a reaction temperature and pressure of the pre-reformer 11 included in the first step are preferably in the range of 450° C. to 650° C. and in the range of 2.5 bar to 30 bar, respectively.

Since a reaction rate and conversion into methane are low when the reaction is achieved at the reaction temperature of the pre-reformer 11 which is lower than a lower limit value, it is not preferable and since carbon deposition occurs when the reaction is achieved at the reaction temperature of the pre-reformer 11 which is higher than an upper limit value, it is not preferable.

Since a volume and a linear velocity of reaction gas increase when the reaction is achieved at the reaction pressure of the pre-reformer 11 which is lower than a lower limit value, it is not preferable in terms of process efficiency and since device configuration cost increases when the reaction is achieved at the reaction pressure of the pre-reformer 11 which is higher than an upper limit value, it is not preferable.

In the synthesis gas preparing step which is the second step, a reformer 13 disposed on the rear end portion of the pre-reformer 11 is used and the reformer 13 is connected to the rear end portion of a pre-heater (a heat exchanger of E-105B in FIGS. 1A and 1B and 2A and 2B and a heat exchanger of E-105 in 3A and 3B).

The reformer 13 included in the synthesis gas preparing step receives the product of the pre-reformer 11 and produces synthesis gas (synthesis gas of carbon monoxide and hydrogen) through methane reforming equations (1) and (2) given below therefrom.

Steam Reforming of Methane (SRM)

$$CH_4+H_2O \rightarrow 3H_2+CO \quad \Delta H=226 \text{ kJ/mol} \quad (1)$$

Carbon Dioxide Reforming of Methane (CDR)

$$CH_4+CO_2=2H_2+2CO \quad \Delta H=261 \text{ kJ/mol} \quad (2)$$

In this case, the catalyst is used, which is selected from the group consisting of nickel, ruthenium, rhodium, palladium, iridium, platinum, and a mixture thereof and the reaction temperature and the reaction pressure of the reformer 13 are preferably in the range of 600° C. to 1200° C. and in the range of 1 bar to 20 bar, respectively and a space velocity is preferably in the range of 1,000 $h^{-1}$ to 500,000 $h^{-1}$.

Since the conversion rate of methane and carbon dioxide is low when the reaction is achieved at the reaction temperature of the reformer 13 which is lower than the lower limit value, it is not preferable and since a high-temperature reformer material is required when the reaction is achieved at the reaction temperature of the reformer 13 which is higher than the upper limit value, it is not preferable.

Further, since heat transfer efficiency deteriorates and the volume and the linear velocity of the reaction gas increase when the reaction is achieved at the reaction pressure of the reformer 13 which is lower than the lower limit value, it is not preferable in terms of process efficiency and since a reaction conversion is limited by equilibrium and reaction conversion rate thus decreases when the reaction is achieved at the reaction pressure of the reformer 13 which is higher than the upper limit value, it is not preferable.

During the synthesis gas preparing process, the methane conversion rate is preferably in the range of 80% to 99% and carbon dioxide conversion rate is preferably in the range of 40% to 60%.

In the methanol preparing step which is the third step, a methanol synthesis reactor 15 is used, which is connected to the rear end portion of the reformer 13 and the methanol synthesis reactor 15 synthesizes the methanol by using the synthesis gas supplied from the reformer 13 as the raw material.

A primary reaction of the methanol preparing step is a hydrogenation reaction of carbon monoxide and carbon dioxide by the metal catalyst. The metal catalyst may be selected from the compound group consisting of mixed metal or mixed oxide such as copper, zinc, aluminum oxide, cerium oxide, zirconium oxide.

In general, in the methanol synthesis reaction, $CO_2$ as well as CO is hydrogenated to produce methanol and, as a result, the yield of the methanol is improved in a composition of synthesis gas in which a predetermined amount of $CO_2$ is included as compared with a composition of synthesis gas in which only CO and $H_2$ coexist. In the synthesis gas injected into the methanol synthesis reactor 15 of the methanol synthesis process, the mole ratio value of $H_2/(2CO+3CO_2)$ and the mole ratio value of $CO_2/(CO+CO_2)$ are preferably in the range of 0.9 to 1.5 and in the range of 0.3 to 0.8, respectively.

When the mole ratio value of $H_2/(2CO+3CO_2)$ is less than a lower limit value, the conversion rate and the reaction rates of carbon monoxide and carbon dioxide decrease and a catalyst life-span is shortened, and as a result, it is not preferable. When the mole ratio value of $H_2/(2CO+3CO_2)$ is more than an upper limit value, hydrogen gas is surplus and a heat duty required for the reformer 13 is large, and as a result, it is not preferable.

When the reaction is achieved at the mole ratio value of $CO_2/(CO+CO_2)$ which is less than a lower limit value, the reaction rate decreases and a methanol synthesis yield thus decreases and there is no $CO_2$ utilization or little $CO_2$ utilization, and as a result, it is not preferable. When the reaction is achieved at the mole ratio value of $CO_2/(CO+CO_2)$ which is more than an upper limit value, the reaction rate of carbon dioxide decreases and the methanol yield thus significantly decreases, and as a result, it is not preferable.

In the third step, the temperature and the pressure of the methanol synthesis reaction are preferably in the range of 200° C. to 400° C. and in the range of 30 bar to 100 bar, respectively and the space velocity is preferably in the range of 1000 $h^{-1}$ to 10000 $h^{-1}$.

In the methanol synthesis reaction, when the reaction is achieved at the temperature which is lower than the lower limit value, the conversion of the reaction gas is insufficient and when the reaction is achieved at the temperature which is more than the upper limit value, the methanol yield decreases by a thermodynamic equilibrium limit, and as a result, it is not preferable.

Further, in the methanol synthesis process, the carbon monoxide conversion is preferably in the range of 50% to 80% and the carbon dioxide conversion is preferably in the range of 5% to 20%.

Next, the product generated by the methanol synthesis reaction in the third step and the unreacted material are separated from each other by using a gas-liquid separator 17 and to this end, the separator 17 is installed on the rear end portion of the methanol synthesis reactor 15 and a gas-phase product and a liquid-phase product transferred from the methanol synthesis reactor 15 are separated from each other by the separator 17.

That is, the present invention includes a process that separates the methanol synthesized by the methanol synthesis reactor 15 by using the separator 17 and the separator 17 separates and discharges liquid-phase methanol which is a target final product and gas (unreacted synthesis gas) including residual unreacted materials.

Simultaneously, some of the emitted gas in which the methanol is separated from the separator 17, that is, some of gas including the unreacted material is recycled to the methanol synthesis process of the third step to be reused as the raw material for the methanol synthesis reaction.

To this end, a splitter 19 is installed on the rear end portion of the separator 17, which splits some of emission gas, which is finally emitted, to the methanol synthesis reactor 15 to recirculate some of emission gas.

The emission gas emitted from the separator 17 includes the unreacted material which may be used as the raw material of the methanol synthesis reaction, and as a result, some of the emission gas which is finally emitted is recycled to the methanol synthesis process of the third step to be reused as the raw material.

Therefore, the raw material may be efficiently used and reduction of a raw material supply amount and the increase in production yield may be achieved.

Further, in the preferred embodiment, the splitter 19 splits some of the high-temperature emission gas transferred from the separator 17 to the methanol synthesis reactor 15 to recirculate the some high-temperature emission gas and some of the residual of the high-temperature emission gas is split again, supplied after being mixed with the natural gas used as the fuel in the heating furnace (heater) 14 installed in the reformer 13, and then is combusted, and the post-combustion gas emitted from the heating furnace 14 is configured to pass through heat exchangers (reference numerals E-101 to 104, E105A, E105B, and E-108) to be described below.

The heating furnace 14 is a component for heating the reforming reactor 13 to raise and maintain the temperature of the reforming reactor to a process demand temperature and supplying the heat required for the reaction, and unreacted material gas emitted in the methanol synthesis process is mixed with the natural gas to be used as the fuel and the heating furnace 14 heats the reforming reactor 13 by using combustion heat generated by combusting the mixed fuel mixed with the unreacted material gas by supplied air.

Further, the high-temperature post-combustion gas emitted from the heating furnace 14 sequentially passes through a plurality of heat exchanges E-101 to 104, E105A, E105B, and E-108 to be described below.

The heat exchangers increase the temperatures of the supplied raw material and the temperature of combustion air through heat exchange with the post-combustion gas and since the post-combustion gas is used as a heat exchange medium for controlling the temperatures of the raw material and the air in the heat exchangers, it is possible to efficiently use energy.

As described above, after methanol and water as final products are condensed and separated from the unreacted materials through a general gas-liquid separation process thereafter, a significant amount of the unreacted material is recycled to the methanol synthesis reactor 15 and some of the unreacted materials is purged to be used for combustion in the heating furnace 14.

Further, since the unreacted gas which discharges from the gas-liquid separator 17 includes inert methane and nitrogen, some amount needs to be purged and some purged gas is recycled to the reformer 13 to be mixed with the raw material.

In this case, carbon efficiency and energy efficiency in an integrated reaction process are maximized through appropriate control on a purge ratio (=Flow rate of stream '231'/Flow rate of stream '220', herein, referring to FIGS. 1A and 2A for stream '231' and stream '220'), the amount of the purged unreacted gas (stream '231') is set to the mole flow ratio of 0.005 to 0.1 with respect to the entire unreacted gas (stream '220'), and the amount of the unreacted gas (stream '233') to be combusted in the heating furnace 14 is set to the mole flow ratio of 0.005 to 0.1 with respect to the entire unreacted gas (stream '220'), and as a result, maximizing reuse rate of the synthesis gas in the methanol synthesis reactor 15 is advantageous in terms of the energy efficiency and the carbon efficiency of the whole integrated process.

When a ratio which is not recycled to the methanol synthesis reactor 15 but purged is less than 0.005, the methane and the nitrogen which are the inert gas are accumulated in the methanol synthesis reactor to decrease the efficiency of the methanol synthesis reactor and when the purge ratio is more than 0.1, the amount of a methanol synthesis reaction material decreases, and as a result, the methanol production amount decreases.

Further, even though the recycling amount of the unreacted material is changed within the range, in the case of the synthesis gas injected into the methanol synthesis reactor 15 in the methanol synthesis process, it is preferable to operate the overall process such that the mole ratio value of $H_2/(2CO+3CO_2)$ is in the range of 0.9 to 1.5 and the mole ratio value of $CO_2/(CO+CO_2)$ is in the range of 0.3 to 0.8 in terms of maximizing the energy and carbon efficiency.

Even though the concentration of $CO_2$ in the reaction feed increases during the recycling, the carbon efficiency in the methanol synthesis may be increased by appropriately controlling the recycling amount of the unreacted material to maintain the mole ratio value of $H_2/(2CO+3CO_2)$ and the mole ratio value of $CO_2/(CO+CO_2)$, which are appropriate for the methanol synthesis reaction, in the range of 0.9 to 1.5 and in the range of 0.3 to 0.8, respectively, and resultantly, operating the integrated reaction process by maintaining the above-mentioned recycling ratio becomes a method capable of maximizing the energy and carbon efficiency.

Consequently, according to implementation of the present invention for accomplishing some of the technical objects, the methanol manufacturing process according to the present invention is configured to include:

(1) a first step of preparing the mixed gas by converting the $C_{2+}$ hydrocarbon included in the natural gas by using the steam and the natural gas as the fuel over the metal catalyst;

(2) a second step of preparing the synthesis gas comprising carbon monoxide, carbon dioxide, hydrogen, and the like in the reformer 13 with the gas which is introduced from the first step and preparing the synthesis gas by injecting carbon dioxide of which the mole ratio is in the range of 0.1 to 0.4 to the natural gas as the raw material;

(3) a third step of synthesizing the methanol from the synthesis gas under a predetermined temperature and pressure; and (4) a step of separating the methanol and the synthesis gas of the unreacted material which are the products in the third step, recycling the unreacted synthesis gas only to the methanol synthesis reactor 15 (the third step) at an appropriate ratio or recycling the unreacted synthesis gas to both the reforming reactor 13 (the second step) and the methanol synthesis reactor 15 (the third step) to allow the unreacted synthesis gas to be reacted again, and mixing and combusting some unreacted gas together with the natural gas injected as the fuel in the heating furnace 14 to supply the heat required for the reforming reactor 13 and resultantly to increase the energy efficiency of a manufacturing process.

It is disclosed that carbon dioxide is injected into the reforming reaction (reforming reactor 13) for preparing the synthesis gas in step (2), or carbon dioxide may be injected into the process after the reforming reaction, that is, the methanol synthesis reaction process (methanol synthesis reactor 15) in which the methanol is synthesized or appropriately split and simultaneously injected into both the reforming reaction for preparing the synthesis gas and the methanol synthesis reaction process.

A high-efficiency methanol preparing process which emits low carbon by efficient carbon dioxide utilization in production and conversion parts of the synthesis gas according to the present invention will be described below in detail with reference to the schematic views of FIGS. 1A and 1B.

Referring to FIGS. 1A and 1B, the pre-reformer 11 of the mixed gas preparing process, the reformer 13 of the synthesis gas preparing process, the methanol synthesis reactor 15 of the methanol synthesis process, the separator 17, the splitter 19, and the heat exchangers E-101 to E-104, E-105A, E-105B, and E-108 are illustrated.

In a configuration of FIG. 1A, the natural gas and the steam are mixed by a mixer M-103 and heat exchanged through the heat exchanger E-103, thereafter, supplied to the pre-reformer 11 and the mixed gas prepared by the pre-reformer 11 and additionally injected carbon dioxide are mixed by a mixer M-101 and heat exchanged through the heat exchanger E-105A, thereafter, supplied to the reforming reactor 13 of the synthesis gas preparing process.

When natural gas (NG) and steam ($H_2O$) are fed as the raw materials in the mixed gas preparing process (first step), and carbon dioxide ($CO_2$) is fed as a component included in the injected natural gas together, the mole ratio of $H_2O/NG$ and the mole ratio of $CO_2/NG$ are preferably in the range of 1.3 to 3.0 and in the range of 0.1 to 0.4, respectively.

Since the carbon deposition occurs in the reforming reactor when the gas is supplied at the mole ratio of $H_2O/NG$ which is less than a lower limit value, it is not preferable and since loss of hydrogen is large in the emission gas when the gas is supplied at the mole ratio which is more than an upper limit value, it is not preferable.

Since the utilization of carbon dioxide is low when the gas is supplied at the mole ratio of $CO_2/NG$ which is lower than the lower limit value, it is not preferable and since the conversion rate of carbon dioxide in the methanol synthesis reactor 15 decreases when the gas is supplied at the mole ratio of $CO_2/NG$ which is more than the upper limit value, it is not preferable.

Further, carbon dioxide may be additionally injected by a scheme that additionally injects carbon dioxide to the synthesis gas production part of the second step (see FIGS. 1A and 1B), a scheme that directly additionally supplies carbon dioxide to the methanol synthesis part of the third step, or a scheme that simultaneously additionally supplies carbon dioxide to the synthesis gas production part and the methanol synthesis part (see FIGS. 2A and 2B).

In the pre-reformer 11, most $C_{2+}$ hydrocarbon which exists in stream '104' of FIG. 1A is converted into methane by the metal catalyst containing the nickel as an active component.

The reaction temperature and pressure of the pre-reformer 11 are in the range of 450° C. to 650° C. and in the range of 2.5 bar to 30 bar, respectively.

Since the reaction rate and the conversion rate into methane are low when the reaction is achieved at the reaction temperature of the pre-reformer 11 which is lower than a lower limit value, it is not preferable and since the carbon deposition occurs when the reaction is achieved at the reaction temperature of the pre-reformer 11 which is higher than an upper limit value, it is not preferable.

Further, since the volume and the linear velocity of the reaction gas increase when the reaction is achieved at the reaction pressure of the pre-reformer 11 which is lower than a lower limit value, it is not preferable in terms of process efficiency and since equipment cost increases when the reaction is achieved at the reaction pressure of the pre-reformer 11 which is higher than an upper limit value, it is not preferable.

In the reforming reactor 13 of the synthesis gas preparing process of the second step, steam reforming and carbon dioxide reforming of the natural gas occur. The product from the reforming reactor 13 exchanges heat with water (water discharged from a steam drum of D-101) in the heat exchanger (reference numeral E-106 in FIG. 1A and not illustrated in FIG. 1B) and thereafter, a coolant is recovered to the steam drum of D-101 again.

The reformer 13 produces the synthesis gas (carbon monoxide and hydrogen) through the reforming reaction of the natural gas using the products from the pre-reformer 11 as raw materials. Further, the reaction temperature and pressure of the reformer 13 are in the range of 600° C. to 1200° C. and in the range of 1 bar to 20 bar, respectively.

Since the conversion rates of methane and carbon dioxide are low when the reaction is achieved at the reaction temperature of the reformer 13 which is lower than the lower limit value, it is not preferable and since a high-temperature reformer material is required when the reaction is achieved at the reaction temperature of the reformer 13 which is higher than the upper limit value, it is not preferable.

Further, since heat transfer efficiency deteriorates and the volume and the linear velocity of the reaction gas increase when the reaction is achieved at the reaction pressure of the reformer 13 which is lower than the lower limit value, it is not preferable in terms of process efficiency and since the reaction conversion decreases due to the reaction equilibrium limitation when the reaction is achieved at the reaction pressure of the reformer 13 which is higher than the upper limit value, it is not preferable.

In the synthesis gas preparing process, the synthesis gas which becomes the raw material in the methanol synthesis process is produced and in FIG. 1A, the flow of the reaction material from the reformer is expressed as stream '111' (Syngas).

The stream '111' (Syngas) primarily includes carbon monoxide, hydrogen, and carbon dioxide and is supplied to the methanol synthesis reactor 15 after compression and pre-heating and in this case, the mole ratio of $H_2/(2CO+3CO_2)$ and the mole ratio of $CO_2/(CO+CO_2)$ are preferably in the range of 0.9 to 1.3 and in the range of 0.1 to 0.4, respectively.

When the mole ratio value of $H_2/(2CO+3CO_2)$ is less than the lower limit value, a reverse water gas reaction is insufficient and the conversion rate of carbon dioxide thus decreases and carbon efficiency decreases and a methanol synthesis catalyst life-span is shortened, and as a result, it is not preferable. Further, when the mole ratio value of $H_2/(2CO+3CO_2)$ is more than the upper limit value, hydrogen gas is unnecessarily consumed and the heat duty of the reformer in order to prepare an excessive amount of hydrogen is large, and as a result, it is not preferable.

When the reaction is achieved at the mole ratio value of $CO_2/(CO+CO_2)$ which is less than the lower limit value, the reaction rate decreases and the methanol synthesis yield thus decreases in the methanol synthesis step and there is no $CO_2$ utilization or little $CO_2$ utilization, and as a result, it is not preferable. Further, when the reaction is achieved at the mole ratio value of $CO_2/(CO+CO_2)$ which is more than the upper limit value, the reaction rate of carbon dioxide decreases and the methanol yield thus significantly decreases and a significant expansion in the size of the methanol synthesis reactor is required, and as a result, it is not preferable.

The primary reaction of the methanol synthesis reactor 15 is the hydrogenation reaction of carbon monoxide and carbon dioxide over the metal catalyst. The metal catalyst may be selected from the compound group consisting of mixed metal or mixed oxide such as copper, zinc, aluminum oxide, cerium oxide, zirconium oxide.

In the third step, the temperature and the pressure of the methanol synthesis reaction are preferably in the range of 200° C. to 400° C. and in the range of 30 bar to 100 bar, respectively.

In the methanol synthesis reaction, when the reaction is achieved at the temperature which is lower than the lower limit value, the conversion of the reaction gas is insufficient and when the reaction is achieved at the temperature which is more than the upper limit value, the methanol yield decreases by the thermodynamic equilibrium limit, and as a result, it is not preferable.

Next, the product flow of the methanol synthesis reaction, that is, stream '215T1→217→218' of the rear end portion of the methanol synthesis reactor 15 is injected into the separator 17 in order to separate a gas-phase product and a liquid-phase product. The separator 17 separates the product of the methanol synthesis into a gas-phase flow composed of the unreacted synthesis gas, that is, stream '220' and a liquid-phase flow primarily composed of methanol and water, that is, stream '17' (Crude MeOH).

In reusing the separated unreacted gas, some is recalculated to the methanol synthesis reactor 15 (stream '221'), some other gas is recycled to the reformer 13 (stream '232'), and some residual gas is supplied to the heating furnace 14 (stream '233') and combusted together with the fuel natural gas fuel to supply the heat required for the synthesis gas production part, that is, the reforming reaction. An emission ratio of the unreacted synthesis gas to the heating furnace 14 for heating the reformer 13 is preferably a mole flow ratio of 0.005 to 0.1 with respect to the entire unreacted gas.

When the split ratio is lower than a lower limit value, the inert gases such as methane and nitrogen which are accumulated in the methanol synthesis reactor 15 and resultantly lower the efficiency of the methanol synthesis reactor 15 and when the split ratio is more than an upper limit value, the amount of the methanol synthesis raw material decreases, and as a result, the methanol production amount decreases.

Meanwhile, the configuration illustrated in FIGS. 2A and 2B is not different from the configuration of FIGS. 1A and 1B except that an additional injection position of carbon dioxide is in the methanol synthesis process part. According to the configuration of FIGS. 2A and 2B, the concentration of carbon dioxide in the methanol synthesis reactor 15 may increase, and as a result, the conversion rate of carbon dioxide in the low-temperature methanol synthesis reaction does not increase but the heat duty at the high temperature for reforming carbon dioxide in the reformer 13 is reduced, thus the process efficiency increases. Further, the temperature of the reactor 15 may be comparatively smoothly controlled due to the reduction of a heat emission amount in the methanol synthesis reaction.

In the configuration of FIGS. 1A and 1B and the configuration of FIGS. 2A and 2B, the plurality of heat exchangers E-101 to 104, E105A, E105B, and E-108 are used and the heat exchangers are disposed along a path of the post-combustion gas so that the post-combustion gas and other materials can exchange heat while high-temperature gas is emitted after the fuel gas which flows into the heating furnace 14 installed outside the reformer 13 is combusted.

Therefore, some of the emission gas emitted from the methanol synthesis reactor 15 of the methanol synthesis process is mixed with the fuel natural gas and combusted in the heating furnace 14 and thereafter, sequentially passes through the heat exchangers. That is, the mixed emission gas of the product emitted from the methanol synthesis reactor 15 and the unreacted material are subjected to gas-liquid separation by the separator 17 and some unreacted gas split by the splitter 19 is combusted together with the fuel natural gas in the heating furnace 14 and thereafter, sequentially passes through the heat exchangers E-101 to 104, E105A, E105B, and E-108.

Regarding the configurations of the heat exchangers, a group of the heat exchangers installed along on the path of the post-combustion gas includes heat exchangers E-105A and E-105B for increasing the temperature of the mixed gas supplied from the pre-reformer 11 to the reformer 13, heat exchangers E-104 and E-108 for controlling the temperature of the post-combustion gas, a heat exchanger E-103 for increasing the temperature of the raw material in advance, and a heat exchanger E-101 for increasing the temperature of the air for combustion, which is supplied to the heating furnace 14.

In this case, the heat exchanger for increasing the temperature of the mixed gas may become a plurality of heat exchangers E-105A and E-105B disposed on the mixed gas supplying path between the pre-reformer and the reformer and the mixed gas supplied from the pre-reformer 11 to the reformer 13 sequentially passes through the plurality of heat exchangers E-105A and E-105B, and as a result, the respective heat exchangers E-105A and E-105B sequentially increase the temperature of the mixed gas through heat exchange between the mixed gas and the post-combustion gas.

As illustrated in FIG. 1B, the heat exchanger for increasing the temperature of the mixed gas may include a first heat exchanger E-105A disposed on the rear end portion of the pre-reformer 11 and a second heat exchanger E-105B disposed on a front end portion of the reformer 13 on the mixed gas supplying path.

In this case, the second heat exchanger E-105B is disposed at an upstream side and the first heat exchanger E-105A is disposed at a downstream side based on the post-combustion gas path and the post-combustion gas sequentially passes through the second heat exchanger E-105B and the first heat exchanger E-105A and on the contrary, the mixed gas emitted from the pre-reformer 11 sequentially passes through the first heat exchanger E-105A and the second heat exchanger E-105B.

The first heat exchanger E-105A allows the mixed gas and the high-temperature post-combustion gas to exchange heat on the rear end portion of the pre-reformer 11, and primarily increases the temperature of the mixed gas and controls the temperature and the pressure of the mixed gas to 500° C. to 700° C. and 1 bar to 20 bar and supplies the mixed gas of which the temperature and pressure are controlled and sent to the second heat exchanger E-105B.

The second heat exchanger E-105B allows the mixed gas passing through the first heat exchanger E-105A and the post-combustion gas to exchange heat on the front end portion of the reformer 13, and secondarily increases the temperature of the mixed gas passing through the first heat exchanger E-105A and controls the state of the mixed gas to 600° C. to 800° C. and 1 bar to 20 bar.

Further, in the examples of FIGS. 1A and 1B in which carbon dioxide is additionally introduced into the synthesis gas production part of the second step, the second heat exchanger E-105B may be used even as a heat exchanger for increasing the temperature of carbon dioxide additionally introduced as the raw material in advance.

That is, the second heat exchanger E-105B is used as a heat exchange for increasing the temperature of the raw material, and carbon dioxide passes through the second heat exchanger E-105B and thereafter, is supplied to the reformer 13 of the synthesis gas preparing process and carbon dioxide is heated through heat exchange with the post-combustion gas while passing through the second heat exchanger E105B.

In addition, a heat exchanger for controlling the temperature of the post-combustion gas may be disposed at the downstream side of the second heat exchanger E-105B based on the post-combustion gas path and as illustrated in FIG. 1B, a plurality of heat exchangers for controlling the temperature of the post-combustion gas, that is, a third heat exchanger E-108 at the upstream side and a fourth heat exchanger E-104 at the downstream side thereof may be sequentially disposed along the post-combustion gas path.

Further, a fifth heat exchanger E-103 for increasing, in advance, the temperature of the raw material in the pre-reformer 11, that is, the temperatures of the natural gas and the steam, is disposed on the front end portion of the pre-reformer 11 and fundamentally, the heat exchanger E-103 may be disposed at the downstream side of the first heat exchanger E-105A and the second heat exchanger E-105B based on the post-combustion gas path.

In particular, the fifth heat exchanger E-103 is disposed at the downstream side of the exchangers for controlling the temperature of the post-combustion gas, that is, the third heat exchanger E-108 and the fourth heat exchanger E-104 and the third heat exchanger E-108 and the fourth heat exchanger E-104 control the temperature of the post-combustion gas to a temperature required by the fifth heat exchanger E-103.

The natural gas and the steam as the raw material are supplied to the pre-reformer 11 through the fifth heat exchanger E-103 and in the fifth heat exchanger E-103, the post-combustion gas of which the temperature is controlled by the third heat exchanger E-108 and the fourth heat exchanger E-104 exchanges heat with the natural gas and the steam as the raw material may be supplied to the pre-reformer 11 in a state in which the temperature of the raw material increases in advance through the heat exchange.

In the fifth heat exchanger E-103, the temperatures and the pressures of the natural gas and the steam are controlled to 400° C. to 600° C. and 1 bar to 20 bar through the heat exchange with the post-combustion gas and thereafter, the natural gas and the steam are supplied to the pre-reformer 11.

The third heat exchanger E-108 and the fourth heat exchanger E-104, which are used for decreasing the temperature of the post-combustion gas to the temperature required by the fifth heat exchanger E-103, receive steam condensate from the steam drum of D-101 illustrated in FIG. 1A and decrease the temperature of the post-combustion gas through the heat exchange of the steam condensate with the post-combustion gas.

As described above, the product from the reformer 13 is cooled by heat exchange with water (coolant) while passing through the heat exchanger (the heat exchanger for controlling the temperature of the synthesis gas) of reference numeral E-106 illustrated in FIG. 1A and the heated coolant passes through the steam drum of D-101 for reuse.

Moreover, some of water split from the steam drum of D-101 through the splitter of B11 is supplied to the third heat exchanger E-108 to be used as the refrigerant (coolant) for controlling the temperature of the post-combustion gas and simultaneously, the high-temperature steam emitted from the steam drum of D-101 is supplied to the fourth heat exchanger E-104 and used as the coolant for additionally controlling the post-combustion gas and thereafter, exported to the outside.

After the temperature of the post-combustion gas decreases through the heat exchange with the refrigerant while the post-combustion gas sequentially passes through the third heat exchanger E-108 and the fourth heat-exchanger E-104, the post-combustion gas passes through the fifth heat exchanger E-103 and in the fifth heat exchanger E-103, the emitted post-combustion gas is used as a heat exchange medium for increasing the temperature of the raw material.

In the third heat exchanger E-108, the coolant is converted into the steam at the state of 200° C. to 400° C. and 30 bar to 50 bar while the cooling water exchanges heat with the post-combustion gas and the steam emitted from the third heat exchanger E-108 is resupplied to the steam drum of D-101 so as to be used as the coolant for cooling the synthesis gas in the heat exchanger of E-106.

In the fourth heat exchanger E-104, the temperature and the pressure of high-pressure steam are controlled to 200° C. to 400° C. and 30 bar to 50 bar and thereafter, the high-pressure steam of which the temperature and pressure are controlled is exported to the outside.

Further, in order to sufficiently supply the water and the steam to the third heat exchanger E-108 and the fourth heat exchanger E-104, the water needs to be supplied to the steam drum of D-101 from the outside, and as a result, the water is heated to the steam state by the heat exchange with the post-combustion gas in a sixth heat exchanger E-102 installed on the post-combustion gas path and thereafter, supplied to the steam drum of D-101.

The sixth heat exchanger E-102 may be installed at the downstream side on the post-combustion gas path, in more detail, at the downstream side of the fifth heat exchanger E-103 so as to allow the post-combustion gas to pass there through and serves to increase the temperature of the water through the heat exchange with the post-combustion gas in advance and supply the water. In the sixth heat exchanger E-102, the water is converted into the steam state of being 200° C. to 400° C. and 1 bar to 5 bar through the heat exchange with the post-combustion gas and supplied to the steam drum of D-101.

Further, in the present invention, the heat exchanger group installed on the post-combustion gas path may further include a seventh heat exchanger E-101 for increasing the temperature of the combustion air in advance, which is supplied to the heating furnace 14 and the seventh heat exchanger E-101 may be installed at the down most stream side on the post-combustion gas path, that is, the downstream side of the sixth heat exchanger E-102.

The combustion air, which is supplied through the seventh heat exchanger E-101, is heated by the heat exchange with the post-combustion gas in the seventh heat exchanger E-101 and thereafter, supplied to the heating furnace 14 installed in the reformer 13 of the synthesis gas preparing process.

In the seventh heat exchanger E-101, the temperature and the pressure of the combustion air, supplied to the heating furnace 14, are controlled to 100° C. to 300° C. and 1 bar to 5 bar.

Figure 3A:
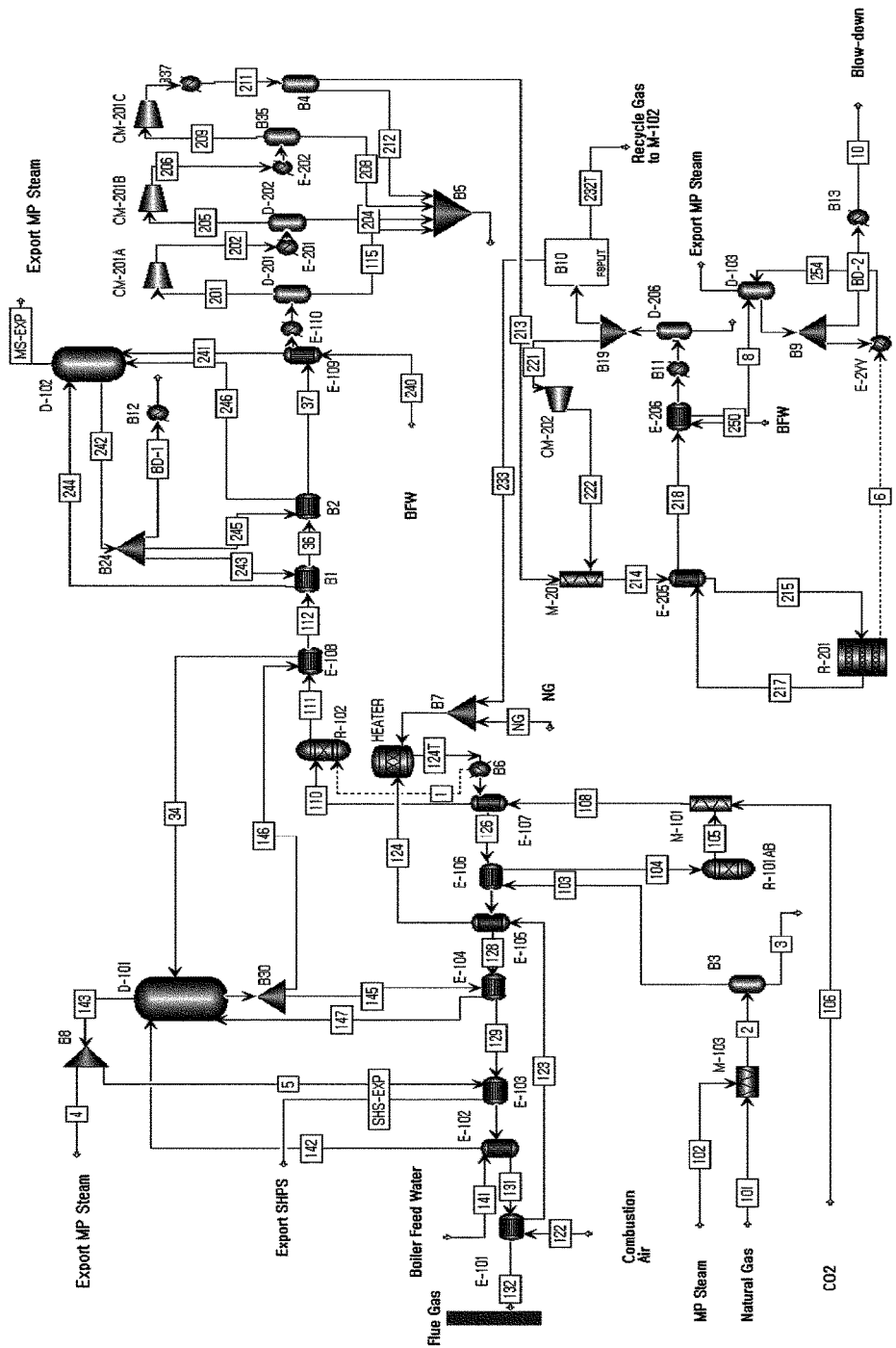
FIGS. 3A and 3B are schematic views illustrating a configuration of optimizing a layout of a heat exchanger in the present invention.
Figure 3B:
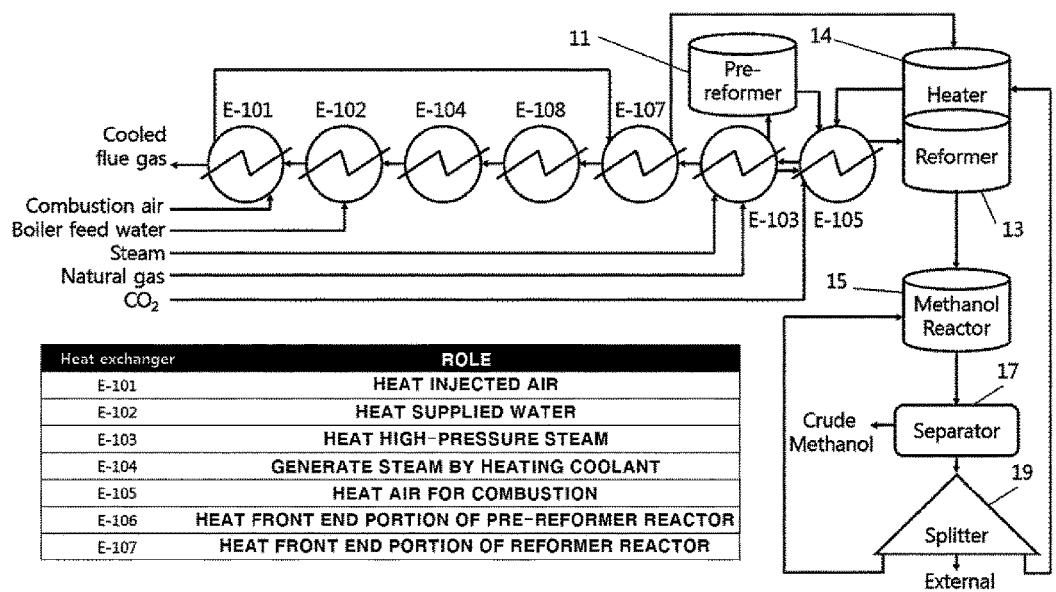

Next, referring to FIGS. 3A and 3B, 3B illustrates primary components in the configuration of FIG. 3A and illustrates the pre-reformer 11 of the mixed gas preparing process, the reformer 13 of the synthesis gas preparing process, the methanol synthesis reactor 15 of the methanol synthesis process, the separator 17, the splitter 19, and the heat exchangers E-101 to E-105, E-107, and E-108.

In the configurations of FIGS. 1B and 2B, the second heat exchanger E-105B, the first heat exchanger E-105A, the third heat exchanger E-108, the fourth heat exchanger E-104, the fifth heat exchanger E-103, the sixth heat exchanger E-102 and the seventh heat exchanger E-101 are disposed sequentially, but in the configurations of FIGS. 3A and 3B, the heat exchanges for increasing the temperature of the mixed gas may be integrated as one heat exchanger.

Hereinafter, in the examples of FIGS. 3A and 3B, an integrated heat exchanger for increasing the temperature of the mixed gas will be referred to as the first heat exchanger E-105 and in the examples in FIGS. 3A and 3B, the first heat exchanger E-105, the fifth heat exchanger E-103, an eighth heat exchanger E-107, the third heat exchanger E-108, the fourth heat exchanger E-104, the sixth heat exchanger E-102 and the seventh heat exchanger E-101 are disposed in order.

The first heat exchanger E-105 is disposed between the pre-reformer 11 and the reformer 13 on the mixed gas supplying path and disposed at the upstream side of the fifth heat exchanger E-103 based on the post-combustion gas path.

The first heat exchanger E-105 allows the mixed gas and the high-temperature post-combustion gas to exchange heat on the rear end portion of the pre-reformer 11, and increases the temperature of the mixed gas and controls the state of the mixed gas to 600° C. to 800° C. and 1 bar to 20 bar and supplies the mixed gas to the reformer 13.

Further, the first heat exchanger E-105 may be used even as a heat exchanger for increasing the temperature of carbon dioxide in advance which is added as the raw material.

That is, the first heat exchanger E-105 may be used even as the heat exchanger for increasing the temperature of the raw material, and carbon dioxide is supplied to the reformer 13 in the synthesis gas preparing process after passing through the first heat exchanger E-105 and heated through the heat exchange with the post-combustion gas while passing through the first heat exchanger E-105.

Although it is described that carbon dioxide is input in the synthesis gas preparing process through the first heat exchanger as above, a method that directly additionally supplies carbon dioxide to the methanol synthesis reactor 15 of the third step may also be adopted similarly to the examples of FIGS. 2A and 2B.

Further, in the examples of FIGS. 3A and 3B, the fifth heat exchanger E-103 for increasing the temperature of the raw material supplied to the pre-reformer 11, that is, the natural gas and the steam as the raw material is disposed at the downstream side of the first heat exchanger and the raw material heated by the heat exchange with the post-combustion gas in the fifth heat exchange E-103 is supplied to the pre-reformer 11.

In the fifth heat exchanger E-103, the temperatures and the pressures of the natural gas and the steam are controlled to 400° C. to 600° C. and 1 bar to 20 bar and thereafter, the natural gas and the steam are supplied to the pre-reformer 11.

The eighth heat exchanger E-107 is disposed at the downstream side of the fifth heat exchanger E-103, which additionally heats the combustion air, of which the temperature increases in the seventh heat exchanger E-101 through the heat exchange with the post-combustion gas and supplies the additionally heated combustion air to the heating furnace 14 installed in the reformer 13 in the synthesis gas preparing process.

In the eighth heat exchanger E-107, the temperature and the pressure of the combustion air are controlled to 400° C. to 600° C. and 1 bar to 5 bar and thereafter, the air of which the temperature and pressure are controlled is supplied to the heating furnace 14.

The third heat exchanger E-108 and the fourth heat exchanger E-104 are disposed at the downstream side of the eighth heat exchanger E-107, which control temperature of the post-combustion gas to a temperature required by the sixth heat exchanger E-102 similarly to the examples of FIGS. 1A and 1B and 2A and 2B.

In this case, fundamental configurations and actions of the third heat exchanger E-108 at the upstream side and the fourth heat exchanger E-104 at the downstream side on the post-combustion gas path are not different from those in the examples of FIGS. 1A and 1B and 2A and 2B, but since the post-combustion gas passing through the fourth heat exchanger E-104 at the downstream side is introduced into the sixth heat exchanger E-102, there is a difference from the examples of FIGS. 1A and 1B and 2A and 2B in that the third heat exchanger E-108 and the fourth heat exchanger E-104 control the temperature of the post-combustion gas to the temperature required by the sixth heat exchanger E-102.

In the third heat exchanger E-108, the coolant is converted into the steam at 200° C. to 400° C. and 1 bar to 30 bar while the coolant exchanges heat with the post-combustion gas and the steam emitted from the third heat exchanger E-108 is resupplied to the steam drum of D-101 so as to be used as the coolant for cooling the synthesis gas in the heat exchanger of E-106.

In the fourth heat exchanger E-104, the temperature and the pressure of high-pressure steam are controlled to 200° C. to 400° C. and 1 bar to 30 bar and thereafter, the high-pressure steam of which the temperature and pressure are controlled is exported to the outside.

Since the sixth heat exchanger E-102 disposed at the downstream side of the fourth heat exchanger E-104 and the seventh heat exchanger E-101 disposed at the downstream side of the sixth heat exchanger E-102 are not different from those in the examples of FIGS. 1A and 1B and 2A and 2B described above, a description thereof will be omitted.

The configuration for preparing methanol has been described with reference to the drawings as above, and as a result, the unreacted gas emitted from the methanol synthesis reactor in the methanol synthesis process is recycled to the methanol synthesis reactor to reduce the supply amount of raw materials and moreover, the unreacted gas is supplied and reused as the fuel of the heating furnace to reduce the process cost.

Further, since heat of the gas emitted after combustion in the heating furnace is used for pre-heating of the reaction material supplied to the pre-reformer and the reformer, pre-heating of the air combustion, or heating of the water supplied as the coolant, it is possible to efficiently use and save the energy.

Moreover, when the high-temperature and high-pressure steam produced by the heat exchangers E-104 and E-108 (heat exchange between the cooling water and the post-combustion gas) by using the heat of the post-combustion gas, the high-temperature and high-pressure steam produced by the heat exchange with the synthesis gas (heat exchange between the high-temperature synthesis gas and the water) on the rear end portion of the reformer, the high-temperature and high-pressure steam acquired by recovering the reaction heat of the methanol synthesis in the heat exchanger attached to the methanol synthesis reactor, and the like are used as the steam as the raw material injected in the process of the first step and residual steam is used to acquire electric power or power required in the overall process, efficiently using the energy may be achieved and the amount of emitted carbon dioxide may be reduced.

In more detail, the heat exchangers (reference numerals E-106, B1, and B2 in FIGS. 1A, 2A, and 3A) through which the high-temperature synthesis gas prepared and emitted by the reformer are disposed on the rear end portion of the reformer 13 and the water is supplied to the heat exchangers to produce the steam from the water by the heat exchange between the high-temperature synthesis gas and the water and thus produced steam can be supplied as the raw material in the process of the first step.

Heat is generated in the methanol synthesis reactor 15 by a exothermic reaction, and when the methanol synthesis reactor 15 is configured as a multi-tubular (boiler) heat exchanger type and a passage which allows the water to pass is configured in an external wall so that reaction heat of the reactor is used as the evaporation heat required for vaporizing water into steam, an internal temperature of the methanol synthesis reactor 15 may be uniformly maintained and the high-temperature and high-pressure steam may be produced by the methanol synthesis reactor 15.

Further, the high-temperature and high-pressure steam produced by the heat exchangers E-104 and E108 by using the heat of the post-combustion gas, the high-temperature and high-pressure steam produced by the heat exchange with the high-temperature synthesis gas by the heat exchangers E-106, B1, and B2 on the rear end portion of the reformer 13, and the high-temperature and high-pressure steam acquired by recovering the methanol synthesis reaction heat by the heat exchanger attached to the methanol synthesis reactor 15 may be used for producing the electric power in addition to being used as the raw material in the process of the first step.

For example, a turbine is installed on the path of the high-temperature and high-pressure steam and the turbine may be rotated by the high-temperature and high-pressure steam and an electric generator is driven by rotational force of the turbine such that the electric power is produced by the electric generator.

The produced electric power may be used as electric power required for the methanol production process and for example, the produced electric power may be used as compressor driving power.

The synthesis gas supplied from the reforming reaction process of the second step to the methanol synthesis process of the third step needs to be supplied after the pressure of the synthesis gas increases to a pressure required in the methanol synthesis reaction and in this case, compressors (reference numerals CM-201A, CM-201B, and CM-201C in FIGS. 1A, 2A, and 3A) are used, which compress, boost, and deliver the synthesis gas.

Further, a compressor (reference numeral CM-202 in FIGS. 1A, 2A, and 3A) for delivering the unreacted synthesis gas is used even for recycling of the unreacted synthesis gas in the methanol synthesis process.

In this case, a compressor motor may be driven by supplying the electric power produced by using the high-temperature and high-pressure steam and the compressor impeller is rotated by driving the compressor motor to use an electric compressor so as to compress and deliver the synthesis gas.

Alternatively, a turbine compressor may be adopted, in which the turbine and the compressor are integratedly connected to one rotary shaft and in the turbine compressor, the high-temperature and high-pressure steam rotates the turbine while passing through the turbine, and as a result, the compressor which is integratedly connected with the turbine through the rotary shaft compresses and delivers the synthesis gas while rotating.

The high-temperature and high-pressure steam produced by the heat of the post-combustion gas, the heat of the synthesis gas, and the reaction heat of the methanol synthesis reaction may be used as the raw material in the process of the first step or for producing the electric power and extensively used for compressing and delivering the synthesis gas (the supplying of the synthesis gas to the methanol synthesis reactor and the recycling of the unreacted synthesis gas).

Hereinafter, advantages of the present invention to convert the natural gas and carbon dioxide into methanol will be described in more detail based on examples.

A carbon mole ratio (S/C ratio) in the steam and the natural gas injected by feed and a mole ratio ($CO_2$/NG) of carbon dioxide and the natural gas are defined to compare a $CO_2$ generation amount (ton) per unit amount (ton) of methanol production according to each example. The $CO_2$ generation amount per unit amount of methanol production is a measure to evaluate the environmentally friendness of a process as the $CO_2$ generation amount per methanol production is smaller for a greener process.

Further, the carbon efficiency is defined as "moles of carbon in the generated methanol/("moles of carbon in 'NG feed+NG fuel')" to compare which process has higher efficiency.

In addition, moles of hydrogen, carbon monoxide, and carbon dioxide in the generated synthesis gas are defined as $H_2$/CO and $H_2$/($2CO+3CO_2$) to compare whether each example is within an appropriate operating range.

Further, the present invention provides the methanol preparing process by the method and respective values are compared with one another by performing a process simulation by using ASPEN PLUS in order to verify the composition in each unit process through modeling.

Example: Comparison of $CO_2$ Generation Amounts Per Unit Amount of Methanol Production in Respective Processes Table 1 shows a simulation result of each process below.

TABLE 1

| Classsification | $CO_2$ injection position | Feed Ratio S/C ratio | $CO_2$/NG | Reformer reactor recirculation ratio (Str232/ Str231) | Purge ratio (Str231/ Str220) | $Co_2$ generation amount/ MeOH production amount | Carbon efficiency (%) | Reactor injection flow (kmol/h/ MeOH-ton production) Reformer reactor (str110) | Methanol synthesis reactor (str215) | $H_2$/CO | $H_2$/ ($2CO + 3CO_2$) |
|---|---|---|---|---|---|---|---|---|---|---|---|
| Com. Ex. | None | 2.500 | 0.000 | 0 | 0.26 | 0.541 | 71.8 | 137.2 | 311.9 | 4.119 | 2.065 |
| Example1 | Reformer reactor | 2.500 | 0.356 | 0 | 0.01 | 0.375 | 78.6 | 99.3 | 374.8 | 3.038 | 1.265 |
| Example2 | Methanol synthesis reactor | 2.500 | 0.356 | 0 | 0.01 | 0.344 | 80.0 | 91.5 | 442.5 | 4.112 | 1.140 |
| Example3 | Reformer reactor | 1.520 | 0.356 | 0 | 0.01 | 0.356 | 79.4 | 75.4 | 368.5 | 2.444 | 1.093 |
| Example4 | Reformer reactor | 1.520 | 0.356 | 0 | 0.02 | 0.359 | 79.2 | 76.5 | 316.9 | 2.445 | 1.124 |
| Example5 | Reformer reactor | 1.520 | 0.356 | 0 | 0.03 | 0.363 | 79.1 | 77.4 | 293.2 | 2.445 | 1.122 |

TABLE 1-continued

| Classsification | $CO_2$ injection position | Feed Ratio S/C ratio | Feed Ratio $CO_2$/NG | Reformer reactor recirculation ratio (Str232/ Str231) | Purge ratio (Str231/ Str220) | $CO_2$ generation amount/ MeOH production amount | Carbon efficiency (%) | Reactor injection flow (kmol/h/ MeOH-ton production) Reformer reactor (str110) | Reactor injection flow (kmol/h/ MeOH-ton production) Methanol synthesis reactor (str215) | $H_2$/CO | $H_2$/ (2CO + 3CO$_2$) |
|---|---|---|---|---|---|---|---|---|---|---|---|
| Example6 | Reformer reactor | 1.520 | 0.356 | 0.92 | 0.06 | 0.360 | 79.3 | 84.0 | 305.5 | 2.527 | 1.327 |
| Example7 | Reformer reactor | 1.520 | 0.356 | 0 | 0.01 | 0.276 | 83.3 | 75.4 | 370.6 | 2.444 | 1.092 |

In Comparative Example, the configurations of FIGS. 1A and 1B are adopted, but as a steam reforming process configured not to inject $CO_2$ in the methanol synthesis process, Comparative Example is compared with another $CO_2$ injection process.

Example 1 shows an example of injecting $CO_2$ into the reformer by applying the configurations of FIGS. 1A and 1B.

Example 2 shows an example of injecting $CO_2$ into the methanol synthesis process by applying the configurations of FIGS. 2A and 2B.

Example 3 shows an example of controlling the reaction material so that the S/C ratio becomes 1.52 by applying the configurations of FIGS. 1A and 1B.

Example 4 shows an example in which the purge ratio is designed to become 0.02 by applying the configurations of FIGS. 1A and 1B.

Example 5 shows an example in which the purge ratio is designed to become 0.03 by applying the configurations of FIGS. 1A and 1B.

Example 6 shows an example in which a ratio of the purge gas to be recycled to the reformer is designed to become 0.92 by applying the configurations of FIGS. 1A and 1B.

Example 7 shows an example considering optimization of a layout of the heat exchangers by applying the configurations of FIGS. 3A and 3B.

Regarding the methanol process according to the examples, as can be seen in Table 1, when $CO_2$ is injected into the reformer as in Example 1, the generation amount of $CO_2$ per unit amount of methanol production is smaller than that of the Comparative Example where $CO_2$ is not injected, and the amount is much smaller when $CO_2$ is injected in the methanol synthesis process as described in Example 2.

Regarding a comparison in the size of the reactor, when $CO_2$ is injected in the methanol synthesis process, flow rate higher than a case where $CO_2$ is injected into the reformer, much higher than the case when $CO_2$ is not injected in the methanol process. As a result, the size of the reactor increases, thereby increasing design cost.

Further, as shown in Examples 3 to 7, when the raw material is injected with the S/C ratio of 1.520 in the methanol process, the $CO_2$ generation amount per unit amount of methanol production is reduced.

In addition, as described by comparing Examples 3, 4, and 5, in the methanol process according to the examples, as the purge ratio increases, the $CO_2$ generation amount (ton) per unit amount (ton) of methanol production increases.

Examples 4 and 6 have the similar carbon efficiency and $CO_2$ generation amount (ton) per unit amount (ton) of methanol production, but in the case of Example 1, since the size of the reactor, which is required for the recycling decreases, Example 6 may be a process which is efficient in terms of cost.

In the methanol preparing process in Examples 1 to 6 according to the present invention, the heat exchangers are disposed as illustrated in FIGS. 1A and 1B and 2A and 2B and contrary to this, Example 7 in which the heat exchanger layout is optimized as illustrated in FIGS. 3A and 3B is the most environmentally friendly process in which the $CO_2$ generation amount (ton) per unit amount of methanol production (ton) is the lowest as shown in Table 1.

INDUSTRIAL APPLICABILITY

As an alternative to global warming, the Kyoto Protocol on a reduction of $CO_2$ emission came into effect in 2005, it is expected that Korea will become a country that will be obligated to reduce carbon dioxide after 2013, and the importance of developing a technology for economical carbon dioxide emission reduction and energy technology is gradually increasing. In the present invention, a method for synthesizing methanol from natural gas, has been developed, which can optimize carbon efficiency and heat efficiency through minimization of an emission of carbon dioxide per unit methanol production by introducing an appropriate recycling method of an unreacted material and appropriately reusing heat generated in a process while supplying an appropriate amount of carbon dioxide in a methanol production process in which methanol is synthesized from the natural gas and carbon dioxide. Further, primarily produced methanol may become an inducing substance which may produce various induction products such as DME, DMC, bio diesel, and synthesis petroleum and the synthesis gas generated from mixed reforming reaction using carbon dioxide may be used even for a Fisher-Tropsch reaction to significantly contribute to process development for economical utilization of carbon dioxide afterwards.

The invention claimed is:

1. A method for producing methanol, the method comprising:
    a first step of preparing mixed gas by using steam and natural gas supplied to a pre-reformer as raw materials and converting $C_{2+}$ hydrocarbons contained in the natural gas into methane over a catalyst;
    a second step of preparing a synthesis gas including carbon monoxide and hydrogen by reforming the mixed gas in a reformer filled with a reforming catalyst; and
    a third step of a methanol synthesis process, in which methanol is prepared by using the synthesis gas as a raw material and reacting the synthesis gas in a methanol synthesis reactor filled with a methanol synthesis catalyst, wherein carbon dioxide is injected into the reformer of the second step, injected into the methanol synthesis reactor of the third step, or split to be injected into both of the reformer and the methanol synthesis reactor, the methanol product and unreacted synthesis gas are separated, a portion of the separated unreacted synthesis gas is supplied to a heating furnace and combusted together with a natural gas, and the mixed gas supplied to the reformer passes through at least one heat exchanger while post-combustion gas emitted from the heating furnace passes through the at least one heat exchanger to exchange heat between the post-combustion gas and the mixed gas by way of heat exchange.

2. The method of claim 1, wherein the carbon dioxide is injected at a mole ratio of 0.1 to 0.4 with respect to the natural gas used as the raw material in the first step.

3. The method of claim 1, wherein some of residual unreacted synthesis gas other than the unreacted synthesis gas supplied to the heating furnace is simultaneously recirculated to the second step process and the third step process to be reused as the raw material for preparing the synthesis gas and synthesizing the methanol or recirculated only to the third step process to be reused as the raw material for synthesizing methanol.

4. The method of claim 1, wherein the carbon dioxide injected into the reformer of the second step passes through the at least one heat exchanger through which the post-combustion gas passes to supply heat from the post-combustion gas to the carbon dioxide by way of heat exchange.

5. The method of claim 4, wherein the at least one heat exchanger comprises:

a first heat exchanger disposed at an upstream side based on a mixed gas supplying path and disposed at a downstream side based on a post-combustion gas path; and a second heat exchanger disposed at a downstream side based on the mixed gas supplying path and disposed at an upstream side based on the post-combustion gas path, wherein carbon dioxide passing through the first heat exchanger the is heated by way of heat exchange with the post-combustion gas in the first heat exchanger.

6. The method of claim 1, wherein the natural gas and the steam as the raw materials are heated in one of the at least one heat exchanger by way of heat exchange with the post-combustion gas passing through the one of the at least one heat exchanger.

7. The method of claim 6, wherein the at least one heat exchanger comprises a first heat exchanger in which the natural gas and the steam as the raw materials are heated, and a second heat exchanger at an upstream side of the first heat exchanger based on a post-combustion gas path, and the method further comprises:

controlling the temperature of the post-combustion gas by way of heat exchange between the post-combustion gas passing through the second heat exchanger and a refrigerant, wherein the refrigerant comprises at least one of water or steam.

8. The method of claim 7, wherein the at least one heat exchanger further comprises a third heat exchanger disposed at a downstream side of the first heat exchanger based on the post-combustion gas path, and the water is used as the refrigerant to further control the temperature of the post-combustion gas passing through the third heat exchanger.

9. The method of claim 1, wherein air used for combustion is primarily heated while the air passes through one of the at least one heat exchanger by way of heat exchange between the air and the post-combustion gas.

10. The method of claim 9, wherein the at least one heat exchanger comprises a first heat exchanger in which the air used for combustion is primarily heated, and a second heat exchanger, the second heat exchanger disposed at an upstream side of the first heat exchanger based on a post-combustion gas path, the method further comprising:

exchanging heat between the post-combustion gas passing through the second heat exchanger and the air to further heat the primarily heated air.

11. The method of claim 8, wherein the at least one heat exchanger further comprises a fourth heat exchanger at a downstream side of the first heat exchanger based on a post-combustion gas path, the method further comprising:

controlling the temperature of the post-combustion gas by way of heat exchange between the post-combustion gas passing through the fourth heat exchanger and a refrigerant comprising at least one of the water or the steam.

12. The method of claim 11, wherein the water is used as the refrigerant as well as for supplying steam.

13. The method of claim 1, wherein the mole ratio of $H_2/(2CO+3CO_2)$ in the synthesis gas introduced to the methanol synthesis reaction of the third step is controlled to be in the range of 0.9 to 1.5.

14. The method of claim 1, wherein the unreacted synthesis gas supplied to the heating furnace to be combusted in the unreacted synthesis gas emitted in the methanol synthesis reaction of the third step is split so that a mole flow ratio of the unreacted synthesis gas supplied to the heating furnace to be combusted becomes 0.005 to 0.1 with respect to the entire unreacted synthesis gas.

15. The method of claim 7, wherein steam produced through the heat exchange between the post-combustion gas and the water in the second heat exchanger is used as the raw material of the first step.

16. The method of claim 1, wherein the steam of the first step is produced by heating water using the reaction heat generated in the methanol synthesis reaction of the third step.

17. The method of claim 1, further comprising disposing an additional heat exchanger on a rear end portion of the reformer, and producing the steam of the first step from water by heat exchange between the water and synthesis gas emitted from the reformer.

18. The method of claim 11, wherein in the fourth heat exchanger through which the post-combustion gas and the water pass, steam produced through the heat exchange between the post-combustion gas and the water is used as the raw material of the first step.

* * * * *